United States Patent [19]

Kahle, II et al.

[11] Patent Number: 5,449,834

[45] Date of Patent: Sep. 12, 1995

[54] METHOD OF SYNTHESIZING 2,6-DINITRO BENZYL COMPOUNDS

[75] Inventors: Charles F. Kahle, II, McCandless Township, Allegheny County; Raphael O. Kollah, Shaler Township, Allegheny County; Gregory J. McCollum, Hampton Township, Allegheny County, all of Pa.

[73] Assignee: PPG Industries, Inc., Pittsburgh, Pa.

[21] Appl. No.: 274,613

[22] Filed: Jul. 13, 1994

[51] Int. Cl.$^6$ .............................. C07C 205/06
[52] U.S. Cl. ........................ 568/424; 568/423
[58] Field of Search ................. 568/425, 423, 424

[56] References Cited

U.S. PATENT DOCUMENTS

| 3,325,568 | 6/1967 | Richter | 260/930 |
|---|---|---|---|
| 4,551,416 | 11/1985 | Chandross et al. | 430/311 |
| 4,632,900 | 12/1986 | Demmer et al. | 430/323 |
| 4,666,820 | 5/1987 | Chandross et al. | 430/270 |
| 4,975,351 | 12/1990 | Akaki et al. | 430/190 |
| 5,082,976 | 1/1992 | Blank et al. | 568/431 |
| 5,134,054 | 7/1992 | Iwasawa et al. | 430/192 |
| 5,166,036 | 11/1992 | Seio et al. | 430/313 |
| 5,230,984 | 5/1993 | Tachiki et al. | 430/270 |

FOREIGN PATENT DOCUMENTS

| 63-247749 | 10/1987 | Japan . | |
|---|---|---|---|
| 63-146029 | 6/1988 | Japan . | |
| 3-131626 | 6/1991 | Japan . | |
| 3-141357 | 6/1991 | Japan . | |
| 150832 | 1/1962 | U.S.S.R. | 568/424 |

OTHER PUBLICATIONS

Houlihan, F. M., et al., "Synthesis of 4-(t-butoxycarbonyl)-2,6-dinitrobenzyl Tosylate, a Potential One Component Photoacid Generator and Dissolution Inhibitor Solubilizable Through Chemical Amplification," Proceedings of the ACS Division of PMSE, Spring Meeting, 1992, San Francisco, Calif., vol. 66, pp., 38-39.

Chem. Abstracts, 71:40389f, Polycondensation of compounds having methyl or active methylene groups with organic dihalogen compounds (1969).

Cameron, J. F. et al., J. Am. Chem Soc. 113, 4303-4313 (1991) Photogeneration of Organic Bases from o-Nitrobenzyl-Derived Carbamates.

Primary Examiner—Werren B. Lone
Attorney, Agent, or Firm—Dennis G. Millman; Paul S. Chirgott

[57] ABSTRACT

Described is a method of preparing dinitrobis(hydroxymethyl)benzene, useful as a photoreactive monomer, from a derivative of stilbene. Also disclosed is a novel dinitrocarbomethoxybenzaldehyde compound useful as an intermediate.

1 Claim, No Drawings

METHOD OF SYNTHESIZING 2,6-DINITRO BENZYL COMPOUNDS

BACKGROUND OF THE INVENTION

The present invention relates to synthesis of photoactive monomers useful for making positive acting photoresists, and to intermediates produced by the synthesis having additional utilities.

Photoreactive polymers are useful as binder resins in photoresist compositions employed in photodevelopment of dectronic components such as circuit boards and other products. Circuit boards are manufactured in a number of processing steps which rely on the use of photoreactive coatings (or photoresists) photochemically produce a difference in solubility between the photoexposed areas and the unexposed areas. In general, two classes of photoresist exist: positive acting resists and negative acting resists. A positive acting resist becomes more soluble in a developer solution when exposed to actinic radiation, and a negative acting resist becomes less soluble in a developer solution when exposed to actinic radiation. For many applications a positive acting resist is preferred. An object of the present invention is to provide novel positive acting photoresists.

One situation in which positive acting resists are preferred is in the case of circuit boards that have through holes that permit connection of one board to an adjacent board in a stack. These through holes are copper coated and must be protected from etchants. One method to accomplish this is the use of an applied, preformed film which covers the hole and protects the copper from etchants during processing. A more recent development is the electrodeposition of photoresist, and this approach has significant advantages over applied film for coating the copper in the holes with photoresist without plugging. An objective has been to create a positive acting, electrodepositable photoresist which could coat the hole, protecting it from etchants, and then be removed from the hole more easily than negative photoresists. Negative acting resists have disadvantages for protecting through holes because of the inherent difficulties associated with removing a crosslinked material from a small space such as a through hole. Furthermore, there is difficulty in exposing negative photoresist material that is located within a bole in order to crosslink such a resist so that it can protect the copper. With a positive photoresist, on the other hand, the holes need not be exposed since the resist material in the holes does not need to become crosslinked in order to serve its purpose.

Diazo functional moieties such as quinonediazidesulfone derivatives having structures (1) and (2) in which R is typically chlorine (e.g., sufonyl chloride)

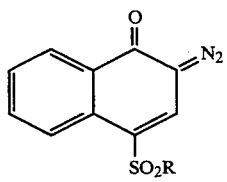

(1)

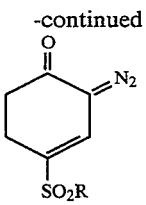

(2)

are well known as photoreactive groups for use in positive acting photoresists. In the synthesis of these prior art compounds, sulfonyl chloride having the structure (1) or (2) is condensed with hydroxyl or amino functionalities attached to monomeric, oligomeric, or polymeric materials. The quinonediazidesulfone derivatives in such a photoresist function by photochemically generating an intermediate ketene which reacts with water to form a carboxylic acid. Photoexposed areas contain salt-forming carboxylic acid groups which dissolve in basic developing solutions. Dissolution of unexposed area in a basic developer is inhibited by the presence of the unreacted hydrophobic components (1) or (2). If water is not present the ketene will react with other hydroxyl groups to form undesirable esters which are not subject to solubilization by a developer. Since the photoreaction mechanism requires the presence of water to work well, a burden is imposed on the user to process the circuit boards under carefully controlled conditions so that the boards all undergo exactly the same dehydration bakes and are handled in very carefully controlled humidity conditions. It would be desirable to have available alternative chemistry for positive acting photoresists that would not entail such precautions.

Many of the prior art photosensitive groups for positive photoresists include molecular groups that are hydrolytically sensitive, which limits the versatility of these groups for use in electrodepositable formulations, whether cationic or anionic. As reported in U.S. Pat. Nos. 5,166,036; 4,975,351 and 5,134,054 the storage stability of electrodepositable photoresists based on diazo containing derivatives of structure (1) or (2) is poor. Examples of other hydrolytically unstable groups include acetals, polyesters, t-butoxycarbonyl (t-BOC) protected carboxylates or phenols, and sulfonate esters. When a cationic or an anionic dispersion is electrodeposited on a conductive substrate, a pH of 12 to 14 or 1 to 2, respectively, may be created at the interface of the coating and the substrate. It is well known that diazo functionalities are sensitive to both high and low pH conditions and will react to form undesirable reaction products. The other chemistries such as t-BOC protected groups, acetals, and esters are also subject to hydrolysis under certain conditions of high and low pH, especially under aqueous conditions. Furthermore, stability of the chemistry under coating conditions and post-coating bake conditions is often given little or no consideration in the prior art. After a substrate has been electrocoated it is usually necessary to bake the coating for a sufficient time to allow for complete coalescence as well as evaporation of water and any volatile organic components. In the case of heat-sensitive diazo functional materials, even short bake times at high temperatures can decompose the diazo compounds. The use of long bake times at lower temperatures severely reduces the processing speed for a manufacturer.

The irradiation of photoresist, in the case of circuit board manufacture, often occurs through a glass or plastic cover sheet. Radiation passing through such a cover sheet to reach the photoresist is predominantly that having wavelengths greater than approximately 315 nanometers. The principal wavelength used for irradiation of photoresists is the 365 nanometer wavelength of a mercury vapor ultraviolet lamp. Therefore, a useful photoresist for printed circuit board manufacture is preferably sensitive to radiation having wavelengths greater than 315 nanometers, particularly to radiation in the vicinity of 365 nanometers.

Some prior art approaches to electrodepositable, positive photoresist rely on photo-generated solubilizing groups which are pendant to the main polymer chain of the photoresist polymer. The theoretical maximum quantum efficiency (the number of reactions divided by the number of photons impinging on the photoresist) of such a system is one, i.e., each photon entering the photoresist would ideally result in formation of a solubilizing group. However, the quantum efficiency is usually much less than one. In order to overcome this limitation on quantum efficiency, systems have been developed which rely on photogenerated catalysts so that one photoreaction produces one catalyst which promotes many other reactions. U.S. Pat. No. 5,230,984 uses photogenerated acid catalysts generated by exposures of 800 millejoules per square centimeter, which is a relatively high exposure dosage. Higher photosensitivity permitting lower exposure dosages would be desirable. Also, these prior art systems require a bake following photoexposure, which undesirably increases processing time. The use of a catalyst can also hurt resolution by diffusion into the surrounding polymer and causing reactions outside of the desired regions. Known photo generated catalysts include sulfonate esters of nitrobenzyl alcohol.

A wide variety of nitrobenzyl alcohol structures are theoretically encompassed by generic structures in Japanese Patent Applications 63-146029, 03-131626, 03-141357, and 63-247749. These applications disclose nitro-containing benzyl alcohol derivatives specifically for use in applications employing short wavelength ultraviolet radiation in the region of 248 nanometers. They fail to recognize the surprisingly high photosensitivity at longer wavelengths (particularly 365 nanometers) of certain dinitrobenzyl structures. Furthermore the above-numerated Japanese applications are non-enabling as to a synthesis for the particular dinitro structures of the present invention. The nitrobenzyl alcohol synthesis disclosed in the Japanese publications for other species is not suitable for producing the dinitrobenzyl alcohols of the present invention at practical yield levels. Furthermore, these applications fail to instruct the use of polymers derived from this material in electrodepositable compositions.

Commonly owned, copending U.S. patent application Ser. No. 08/274,614, titled "POSITIVE PHOTOACTIVE COMPOUNDS BASED ON 2,6-DINITRO BENZYL GROUPS" filed on even date herewith by Charles F. Kahle II, Neil D. McMurdie, Raphael O. Kollah, Daniel E. Rardon, and Gregory J. McCollum discloses positive acting photochemistry that yields a substantial improvement in quantum efficiency resulting from the structure of 2,6-dinitro benzyl groups having structure (3):

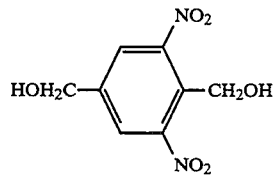

The 2,6-dinitro substitution around a benzyl group is believed to enhance photosensitivity. A polymer containing such a group undergoes chain scission of the backbone polymer to lower molecular weight fragments upon exposure to actinitic radiation. The photochemistry relies on the photooxidation of the benzyl group by the nitro group. Each photoreaction causes at least two changes to the polymer containing the 2,6-dinitro benzyl group—lower molecular weight and formation of a salt forming group—both of which enhance the sensitivity of the photoexposed material to developer. These changes work in concert to give excellent photosensitivities.

Polymers can be prepared from these dinitro diol compounds which are hydrolytically and thermally stable to the processing conditions required for manufacture of circuit boards. Polymers prepared from structure (3), such as polyurethanes are known to be stable in electrocoating baths, thus permitting electrodeposition of these photosensitive polymers. Polyesters have also been prepared with the desirable dinitro diol groups.

Methods of synthesizing the photosensitive dinitro diols of structure (3) would be desirable.

SUMMARY OF THE INVENTION

The present invention is a method of synthesizing dinitro diol compounds of structure (3) which are useful as monomers from which may be polymerized positive acting photochemicals. The novel method of synthesis comprises:
(a) providing dinitro carbomethoxymethoxy stilbene;
(b) ozonolytically cleaving the product of (a) to form dinitrocarbomethoxybenzaldehyde;
(c) reduction of the product of (b) to dinitrocarboisopropoxybenzyl alcohol;
(d) hydrolysis of the product of (c) to dinitrocarboxylbenzyl alcohol; and
(e) reduction of the product of (d) to dinitrobis(hydroxymethyl)benzene.

Another aspect of the invention is the dinitrocarbomethoxybenzaldehyde intermediate product of step (b) above having the structure:

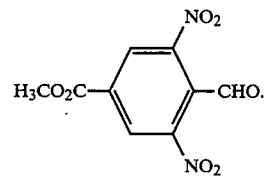

The dinitrocarbomethoxybenzaldehyde has utility for synthesizing photoreactive polymers as well as other dinitro compounds.

DETAILED DESCRIPTION

The starting point of the method of the present invention is a stilbene derivative of structure (4) which may be prepared by the method of Hargreaves and McGookin in *J. Chem Soc. Ind.* 1950, 69, pages 186–191. Examples 1 and 2 illustrate the synthesis of the stilbene derivative (4).

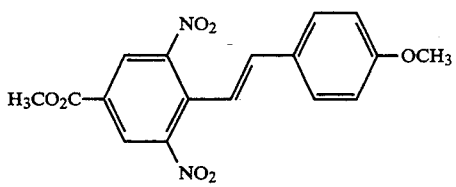

EXAMPLE 1

Synthesis of 3,5-Dinitro-p-methyltoluate

A mixture of 3,5-dinitro-p-toluic acid (497.53 grams), methyl alcohol (2200.0 grams), sulfuric acid (5.0 grams), and trimethylorthoformate (265.3 grams) was heated to reflux for 34 hours. Methyl alcohol (765.0 grams) was distilled off of the reaction mixture and the mixture was allowed to cool slowly to allow the product to precipitate. The mixture was filtered to recover the crystalline product. After drying, crystalline 3,5-dinitro-p-methyltoluate (412.0 grams) was isolated in 83% yield.

EXAMPLE 2

Synthesis of 2,6-Dinitro-4-Carbomethoxy-4'-Methoxystilbene

A mixture of 3,5-dinitro-p-methyltoluate (120.08 grams) from Example 1, p-anisaldehyde (68.08 grams), activated basic alumina oxide (150 mesh, 58 angstrom, 70.00 grams), and ethyl acetate (150.0 grams) was heated to reflux. Piperidine (15.3 grams) was added dropwise over 5 hours and the reaction held at reflux for another 6.5 hours. Upon cooling, a yellow crystalline product precipitated and was isolated by filtration. The crude product was recrystallized once from concentrated ethyl acetate to recover 77.6 grams of bright yellow 2,6-dinitro-4-carbomethoxy-4'-methoxystilbene (4). The product was characterized by NMR and had a melting point of 141.5 to 143° C.

EXAMPLE 3

Synthesis of 2,6-Dinitro-4-Carbomethoxybenzaldehyde by Ozonolytic Cleavage of 2,6-Dinitro-4-Carbomethoxy-4'-Methoxystilbene (4)

Stilbene derivative(4) from Example 2 (10.0 grams) was dissolved in ethyl acetate (705 grams). A portion (200 milliliters) of the solution was added to a reactor and cooled to less than 5° C. A mixture of approximately 4% ozone in oxygen was bubbled through the solution until the solution turned from yellow to colorless, indicating the reaction had gone to completion. The solution was sparged with nitrogen, and the reaction mixture was transferred to a mixture of 0.002% ferric chloride in acetic acid (1 gram), potassium iodide (46.48 grams) and deioinized water (300 grams) to quench the ozonide and hydroperoxide intermediates. This process was repeated until all the starting solution was consumed. This mixture was acidified with concentrated HCl (15.0 grams), sparged with nitrogen and left to stir overnight in a closed jar. The solution was titrated with 0.5M aqueous $Na_2S_2O_3$ (97.2 milliliters) until the iodine color is discharged. The ethyl acetate layer was separated and washed with a mixture of deionized water (100 grams), potassium iodide (5.0 grams), and concentrated hydrochloric acid (5.3 grams). The ethyl acetate layer was separated and washed once with a solution of deioinized water and sodium thiosulfate followed by a final wash with brine solution, separated, and dried with magnesium sulfate. The solution was filtered, and the solvent removed in vacuo. Water (100 gram) was added to the product mixture and stripped in vacuo to steam distill away the p-anisaldehyde by-product. This was repeated twice more to recover 6.2 grams of crude product. Recrystalization from an ethyl acetate/heptane mixture produced 3.2 grams of product (melting point 98°–100° C.). The proton and carbon-13 NMR conclusively identified the product as 2,6-dinitro-4-carboxymethylbenzaldehyde (5).

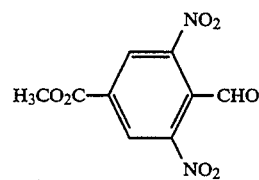

EXAMPLE 4

Reduction of 2,6-Dinitro-4-Carbomethoxybenzaldehyde (5) to 2,6-Dinitro-4-Carboisopropoxybenzyl Alcohol (6)

A mixture of anhydrous 2-propanol (250 grams), aluminum isopropoxide (4.9 grams), and 2,6-dinitro-4-carbomethoxybenzaldehyde (5) (5.6 grams) was heated to reflux for about 40 minutes until the starting material was completely converted (Meerwein-Ponndorf-Verley reduction) to product as determined by thin layer chromatography. The solution was cooled and taken up with ethyl acetate (200 grams). The organic layer was washed with saturated aqueous NaCl, separated, and dried over magnesium sulfate. The organic layer is then filtered and stripped in vacuo to recover 5.2 grams of crystalline product with melting point of 105°–107° C. Proton and carbon NMR spectra were conclusive for 2,6-dinitro-4-carboisopropoxybenzyl alcohol (6).

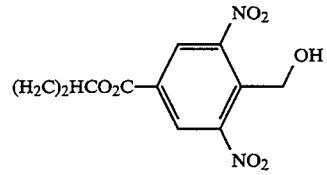

EXAMPLE 5

Hydroylsis of 2,6-Dinitro-4-Carboisopropoxybenzyl Alcohol (6) TO 2,6-Dinitro-4-Carboxybenzyl Alcohol (7)

A solution of sodium hydroxide (0.48 grams) in deionized water (20.0 grams) was added to a 2-propanol (20.0 grams) solution of 2,6-dinitro-4-carboisopropoxybenzyl alcohol (6) (3.05 grams) at room temperature. The reaction was complete in less than an hour as determined by thin layer chromatography. Deionized water (25 grams) was added to the reaction mixture and then acidified with concentrated hydrochloric acid. The solution was extracted twice with ethyl acetate (50 grams). The organic layers were combined, dried over sodium sulfate, filtered, and the solvent removed in vacuo. The product was used without purification in the next step as described in Example 6.

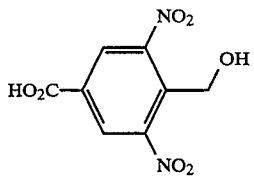
(7)

EXAMPLE 6

Borane Reduction of 2,6-Dinitro-4-Carboxybenzyl Alcohol (7) to 2,6-Dinitrobenzene-1,4-Dimethanol (8)

At room temperature 144 grams of a 1.0M borane solution in tetrahydrofuran (THF) was added dropwise to a THF (50 grams) solution of 2,6-dinitro-4-carboxybenzyl alcohol (7) (16.7 grams) from Example 5. Excess borane-THF solution was necessary to consume residual water. Once the carboxylate was completely reduced, as shown by an infrared spectrum, methyl alcohol (50 grams) was added to quench unreacted hydride. All the solvent was stripped in vacuo. Methyl alcohol (50 grams) was added to the reaction product and stripped again. This process was repeated once more. An amorphous brown solid (13.5 grams) was isolated whose proton and carbon NMR spectra confirmed the product to be 2,6-dinitrobenzene-1,4-dimethanol (8). Light yellow crystals (melting point 124°–125.5° C.) were obtained after recrystalization from water.

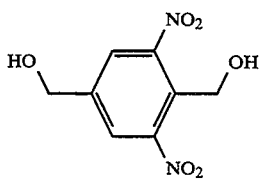
(8)

Examples 7, 8, and 9 demonstrate alternative methods of converting stilbene derivatives to the dinitro diol (8).

EXAMPLE 7

Synthesis of 3,5-Dinitro-p-hydroxymethyltoluene (9)

A solution of aluminum chloride (8.90 grams) in tetrahydrofuran (50.0 grams) was carefully added at 25° C. to a suspension of sodium borohydride (7.60 grams) in tetrahydrofuran (100.0 grams) and diglyme (50.0 grams) under a nitrogen atmosphere forming a milky white suspension. The temperature of the reaction was increased to 50° C., and a solution of 3,5-dinitro-p-toluic acid (22.60 grams) in tetrahydrofuran (110.0 grams) was added over 30 minutes via an addition funnel. The reaction mixture was refluxed for 4 hours at which time the starting acid was converted to the alcohol as determined by thin-layer chromatography. Upon cooling to 25° C., the entire reaction mixture was poured into a flask containing 2% hydrochloric acid (510 grams) which was placed in an ice bath. The contents were transferred to a separatory funnel and extracted with three 150-milliliter portions of ethyl acetate. The organic layers were combined, dried over magnesium sulfate, and vacuum stripped (80° C., 5 mmHg) leaving a light brown, viscous liquid (18.0 grams, 84.9% theoretical) which solidified to a waxy solid upon standing at room temperature. The $^1$H and $^{13}$C NMR spectral data are consistent with the structure of 3,5-dinitro-p-hydroxymethyltoluene (9).

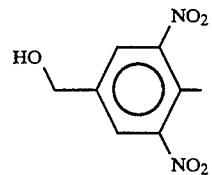
(9)

EXAMPLE 8

Synthesis of 2,6-Dinitro-4-Hydroxymethyl-4'-Methoxystilbene

A solution of 2,6-dinitro-4-hydroxymethyltoluene (9) from Example 7 (3 grams) and hexamethyldisilazane (2.28 grams) in n-butyl acetate (20 grams) was combined with p-anisaldehyde (1.92 grams) and piperidine (0.384 gram) and the mixture was heated to reflux under a N$_2$ blanket for 14 hours The reaction was cooled, concentrated in vacuo and the crude product analyzed by $^1$H NMR to reveal the characteristic AB splitting pattern of the stilbene protons. The product was confirmed by comparison to an authentic sample prepared according to Example 9 using thin layer chromatography and NMR techniques, confirming the presence of structure (10)

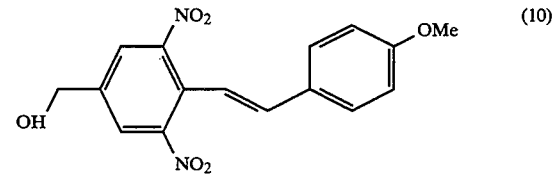
(10)

EXAMPLE 9

Preparation of 2,6-Dinitro-4-Hydroxymethyl-4'-Methoxystilbene from 2,6-Dinitro-4-Carbomethoxy-4'-Methoxystilbene A mixture of 2,6-dinitro-4-carbomethoxy-4'-methoxystilbene (4) (1 gram) and dichloromethane (20 milliliters) was cooled to −78° C. A toluene solution of diisobutylaluminium hydride (8.37 milliliters) was added and the reaction allowed to warm up to −5° C. over 2 hours. The reaction was quenched with water, diluted with dichloromethane, and the organic layer concentrated in vacuo to yield 0.9 grams of crude product (11) as determined by thin layer chromatography (CH2Cl2 as eluent, silica gel, R$_f$=0.5).

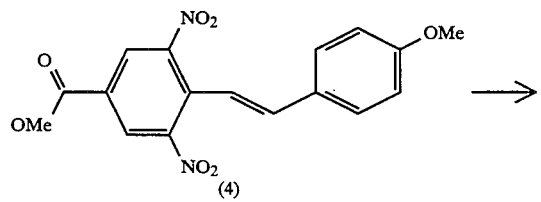
(4)

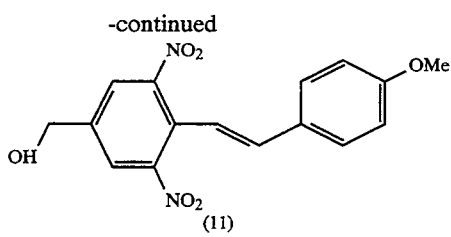

(11)

Polymers

Dinitro diol monomers (8) may be copolymerized with a wide variety of comonomers to produce polymers having the photoactive dinitro groups. A polyurethane can be prepared by the reaction of a diisocyanate with dinitro diol (8) to generate compounds with structure (12):

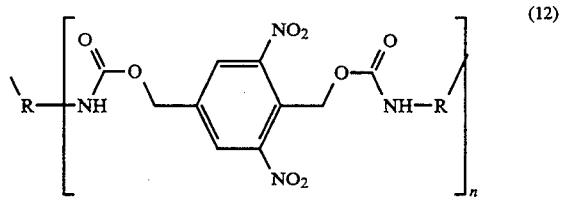

(12)

where n is 1 to infinity and R is the residue of the isocyanate. Example 10 illustrates such a reaction.

Polyesters such as (13) may be produced by condensation of sebacoyl chloride with dinitro diol (8) as illustrated in Example 14.

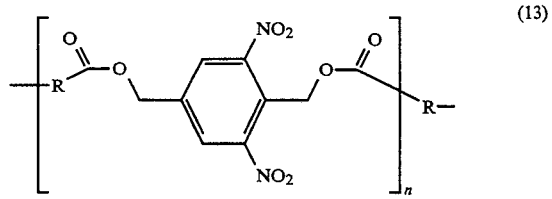

(13)

where n is 1 to infinity, and R is the residue of the sebacoyl chloride or any other acid residue.

EXAMPLE 10

Preparation of Photoreactive Polyurethane (A)

TMXDI® meta-tetramethylxylenediisocyanate from American Cyanamid (18.36 grams) was added dropwise to a 50° C. solution of 2,6-dinitrobenzene-1,4-dimethanol (8) (8.94 grams), N,N-dimethylbenzylamine (0.06 grams), and dibutyltin dilaurate (0.06 grams) in methyl isobutyl ketone (24.0 grams). The reaction was held for 1.5 hours at 60° C. to reach an isocyanate equivalent weight of 703. A solution of PPG 425 (polypropylene glycol, 425 mol. wt., 15.80 grams) and methyl isobutyl ketone (4.00 grams) was then added dropwise over 1 hour, and the reaction held for an additional 6 hours. A trace of isocyanate remained by infrared spectroscopy so 2 drops of 2-butoxyethanol were added to quench the remaining isocyanate. The polyurethane was isolated at room temperature and had a solids content of 67.0%.

EXAMPLE 11

Preparation of Epoxy-Amine Polymer (B)

Bisphenol A diglycidyl ether (446.69 grams) and bisphenol A diol (181.15 grams) were heated to 110° C. in methyl isobutyl ketone (40.00 grams). Ethyltriphenylphosphonium iodide (0.55 grams) was added and the mixture allowed to exotherm to 167° C. and then held at 160° C. for one hour. The reaction mixture was cooled to 110° C. and methyl isobutyl ketone (67 grams) was added to reduce viscosity. A mixture of dibutylamine (24.25 grams) and 2-(methylamino)ethanol (42.25 grams) was added and rinsed into the reactor with methyl isobutyl ketone (15.00 grams). After three hours the resin was cooled to room temperature and retained for later use. The resin was 92.2% solids.

EXAMPLE 12

Cationic Dispersion of Photoreactive Polyurethane (A) and Epoxy-Amine Polymer (B)

Polyurethane A of Example 10 (52.8 grams), epoxy-amine B of Example 11 (46.9 grams), 2-butoxyethanol (4.00 gram), and lactic acid (85%, 3.00 gram) were charged to a dispersion vessel. Deionized water (684 grams) was added slowly at a high stir rate to convert the resins to an aqueous dispersion. The residual methyl isobutyl ketone was stripped off by adding 100 grams of deionized water and stripping off 100 grams of volatiles under vacuum. The resulting dispersion had a particle size of 3970 angstroms and a solids content of 9.3%.

EXAMPLE 13 electrodeposition of an Epoxy-Amine/Urethane Dispersion

An epoxy-amine/urethane dispersion, from Example 12 (9.3% solids), was filtered through a 400 mesh nylon filter (38.1 micron sieve size). The dispersion was heated to 100° F. (38° C.) with constant stirring. 2-Butoxyethanol (10.0 grams) and 2-hexyloxyethanol (6.0 grams) were added. The resin was reduced to 5% solids with deionized water and placed into a cationic electrodeposition bath. A copper clad laminate substrate having ½ oz. copper per square foot (0.105 gram per square centimeter) was pre-cleaned with a detergent solution, followed by rinsing with deionized water and drying. The board was attached to a cathode, lowered into the electrodeposition bath (100° F., 38° C.), and current (80 volts) was applied for 90 seconds. A dehydration bake of 135° C. for 3 minutes yielded 0.26 mil (0.007 millimeter) film build. Voltages ranging from 40 to 110 volts generated film builds from 0.24 mil (0.006 millimeter) to 0.64 mil (0.016 millimeter). The resist was exposed to UV light through a Mylar photomask on an ORC Model HMW-532D UV exposure unit. The presence of the Mylar mask substantially filtered wavelengths below about 315 nanometers. The exposed board was then dipped into a developer consisting of 2.5% lactic acid (85% in water) and 2.5% 2-butoxyethanol in deionized water heated to 88° F. (31° C.) with constant stirring. Development times to remove the photoexposed areas varied with a lower energy photoexposure (150 mJ/cm$^2$) requiring a development time of 2 minutes 20 seconds, and a higher energy (600 mJ/cm$^2$) requiring 1 minute 40 seconds development time.

EXAMPLE 14

Preparation of Photoreactive Polyester

This example illustrates the use of dinitro diol to produce photoactive polyester polymer. Sebacoyl chloride (5.20 grams) was added dropwise to a solution of 2,6-dinitrobenzene-1,4-dimethanol, structure (8) (4.89 grams) and triethylamine (4.15 grams) in tetrahydrofuran (20.00 grams) at room temperature. The reaction mixture was heated to reflux for 30 minutes then cooled to room temperature and filtered to remove precipitated salts. The salts were rinsed with n-butyl acetate. The resin had a solids of 21.4% and structure (13).

EXAMPLE 15

Photoexposure and Development of the Photoreactive Polyester

This example illustrates development of the photoreactive polyester of Example 14. The polyester from Example 14 was drawn down neat with a #20 wire (0.508 millimeter wire diameter) wound drawdown bar onto pre-cleaned, laminated substrate having ½ oz. copper per square foot (0.105 gram per square centimeter), allowed to flash for 10 minutes, and then baked for 3 minutes at 135° C. The post-baked film remained slightly tacky. The resist was exposed through a Mylar photomask with UV light of 424 mJ/cm² energy. An aqueous base developer (2% sodium meta-silicate pentahydrate in deionized water) at 105° F. (40.5° C.) dissolved the photoexposed resist to the copper in 16 minutes with the unexposed film remaining intact.

EXAMPLE 16

Photoexposure and Development of the Photoreactive Polyester with an Acid Functional Copolymer A copolymer of dimethyl maleate and undecylenic acid was synthesized as follows. Dimethyl maleate (216.0 grams) and undecylenic acid (184.0 grams) were charged to a reaction vessel equipped with a mechanical stirrer, thermocouple, condenser, and nitrogen inlet. The mixture was heated to 125° C. under a nitrogen atmosphere, and di-tert-amyl peroxide (8.7 grams) was added via addition funnel over 30 minutes with no exotherm. The reaction was maintained at 125° C. for 11 hours and was then vacuum stripped at 210° C. to remove any unreacted monomers. The contents were cooled, and n-propanol (150 grams) was added to achieve a Gardner-Holdt viscosity of W-X. The resulting yellow resin was measured at 69.5% total nonvolatiles (110° C., 60 minutes), with an acid value of 95.3.

The copolymer derived from the polyester of Example 14 was blended with the copolymer derived from dimethyl maleate and undecylenic acid described above in a ratio of 55% copolymer to 45% polyester. A #20 wire (0.508 millimeter wire diameter) wound drawdown bar was used to coat the resin on a laminated substrate having ½ oz. copper per square foot (0.105 gram per square centimeter), then baked 3 minutes at 135° C. after a 10 minute flash time. The baked, unexposed film was tacky, but after exposure to UV radiation, exposed areas were dissolved readily using the same developer described in Example 15, and the unexposed areas remained unaffected.

The invention has been described with reference to particular embodiments for the sake of providing the best mode of carrying out the invention, but it should be understood that other alternatives and variations known to those of skill in the art may be resorted to without departing from the scope of the invention as defined by the claims which follow.

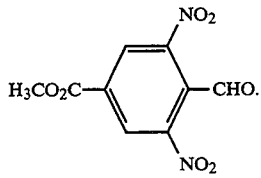

We claim:

1. Dinitrocarbomethoxybenzaldehyde having the structure